United States Patent
Wobus et al.

[11] Patent Number: 6,007,993
[45] Date of Patent: Dec. 28, 1999

[54] IN VITRO TEST FOR EMBRYOTOXIC AND TERATOGENIC AGENTS USING DIFFERENTIATION-DEPENDENT REPORTER EXPRESSION IN PLURIPOTENT RODENT EMBRYONIC CELLS

[75] Inventors: Anna Magdalene Wobus, Gatersleben; Wolfgang-Michael Franz, Gross Grönau, both of Germany

[73] Assignee: Insitut fur Pflanzengenetik und Kulturpflanzenforschung, Gatersleben, Germany

[21] Appl. No.: 08/983,147
[22] PCT Filed: Jun. 27, 1996
[86] PCT No.: PCT/DE96/01183
    § 371 Date: Feb. 24, 1998
    § 102(e) Date: Feb. 24, 1998
[87] PCT Pub. No.: WO97/01644
    PCT Pub. Date: Jan. 16, 1997

[30] Foreign Application Priority Data

Jun. 28, 1995 [DE] Germany .............. 195 25 285

[51] Int. Cl.[6] .............. C12Q 1/68; C07H 21/04
[52] U.S. Cl. .............. 435/6; 435/8; 435/29; 435/441; 435/455
[58] Field of Search .............. 435/6, 8, 29, 441, 435/455

[56] References Cited

U.S. PATENT DOCUMENTS

5,346,812  9/1994  Voellmy et al. .............. 435/6

OTHER PUBLICATIONS

Lai, FASEB J. 9(4), A942 (Apr. 1995).

*Primary Examiner*—Kenneth R. Horlick
*Attorney, Agent, or Firm*—Horst M. Kasper

[57] ABSTRACT

The invention concerns an in vitro test procedure for the detection of chemically induced effects on embryonic development and for differentiation for the purpose of embryotoxicity/teratogenicity screening based on differentiated pluripotent embryonic stem (ES) cells from mice and rats using embryonic germ (EG) cells obtained from primoridial germ cells. The proposed test procedure is characterised in that stable transgenic ES or EG cell clones containing tissue-specific promoters and reporter genes are selected, differentiation-dependent expression of tissue-specific genes is carried out following differentiation of ES cells in the presence of embryotoxic substances acting at specific times into different germination path derivatives; this is followed by detection of chemically induced activation, repression or modulation of tissue-specific genes which regulate embryonic development.

19 Claims, 2 Drawing Sheets

6,007,993

IN VITRO TEST FOR EMBRYOTOXIC AND TERATOGENIC AGENTS USING DIFFERENTIATION-DEPENDENT REPORTER EXPRESSION IN PLURIPOTENT RODENT EMBRYONIC CELLS

The invention relates to an in vitro test procedure for the detection of chemically-induced embryotoxic (for example also teratogenic) effects based on differentiated pluripotent embryonic stem (ES) cells from the mouse and rat and using embryonic germ (EG) cells obtained established from primordial germ cells.

The detection of teratogenic properties of chemical agents occurs at this time by determination of the reproduction toxicity of test substances following single or multi-administrations to pregnant laboratory mammals and by tests of the embryotoxicity in the early stages of pregnancy (Holz and Siegemund, "Der Einsatz von Tieren in der Forschung und Entwicklung im Verbraucher- und Umweltschutz, Abschlussbericht zur Basiserhebung des Batelle-Instituts 1988 {The Use of Animals in the Research and Development in the Protection of the Consumer and the Environment, Final Report to the Base Determination of the Batelle Institute 1988}). Furthermore, in vitro tests are performed with mammal embryos (Neubert and Merker, Cell culture techniques—applicability for studies on prenatal differentiation and toxicity, de Gruyter, Berlin—New York (1981)) and with embryonic organs for teratogenicity tests. These tests procedures have however the disadvantage that they require the use of a large number of live mammals, in particular rats and mice. In vitro test procedures, in which primary cell cultures of limb buds (for example, "Limb Buds", Kochhar, Teratology 11, 273–287 (1975)), or brain parts of embryonic rats (Flint and Orton, Toxicol. Appl. Pharmacol. 76, 383–395 (1984)) or permanent cell lines of embryonic or adult mammal tissue, such as tumor cells of the ovary or embryonic palate cells are employed, do not fulfill, strictly speaking, the requirements which are imposed on the teratogenicity tests during the embryogenesis, namely giving indications of possible disgeneses or developmental disturbances.

Efforts have been made for a couple of years to employ permanent cultures of totipotent/pluripotent embryonic stem cells (ES cells) for the detection of embryotoxic and mutagenic substances (Laschinski et al., Reproductive Toxicol. 5, 57–65 (1991), Newall and Beedles, Toxicol. in Vitro 8, 697–701 (1994), Sehlmeyer and Wobus, Mutation Res. 324, 69–76 (1994)). Embryonic stem cells are the totipotent cells of the early embryo from which there develops the complete mammal organism. Disturbances during the germ-layer and prenatal development can lead to the necrosis of the embryos (preimplantative death), to developmental disturbances, maldevelopment or, respectively, malformations.

There are known as in vitro systems of totipotent or, respectively, pluripotent cells 1. embryonic stem cells (ES cells), permanent lines of totipotent embryonic cells (Evans and Kaufman, Nature 282, 507–509 (1981)), and
2. embryonic germ cells (embryonic germ cells, EG cells), which are obtained from primordial germ cells (PGC) of about 9-day old embryos and are cultivated as permanent cell lines (Stewart et al., Dev. Biol. 161, 626–628 (1994)).

Both ES cells as well as EG cells are totipotent and participate in vivo in the normal embryogenesis after retransfer into the blastocyst and are in the position to colonize the germination path (Bradley et al., Nature Bd. 3 309, 255–256 (1984), Matsui et al., Cell 70, 841–847 (1992)).

ES cells can differentiate in vitro after differentiation in embryo-like aggregates, so-called embryoid bodies, derivatives of all three germ layers, i.e. in cardiogenic cells (Doetschmann et al., J. Embryol. Exp. Morphol. 87, 27–45 (1985)), in myogenic cells (Rohwedel et al., Dev. Biol. 164, 87–101 (1994)), neuronic and haematopoietic cells (Wiles and Keller, Development 111, 259–267 (1991)).

It has been demonstrated in previous experiments that the teratogenic retinoic acid (RA) led to grave changes of the expression of tissue-specific genes if it took effect at specific times of the embryoid body differentiation, and to activation, repression, or modulation of the expression of the myocardial-specific genes or somatic-specific genes (Wobus et al., Roux's Arch. Dev. Biol. 204, 1994 (36–45). This activation, repressing, or modulation of the gene expression can also be made visible through reporter genes, for example X-Gal or luciferase.

Previous in vitro processes with ES cells relate primarily to test procedures for the detection of cytotoxic effectiveness of embryotoxic compounds with the aid of the MTT test (Laschinski et al., see above). In this case, ES cells with higher cytotoxic sensitivity were observed than in differentiated cells.

Tests relative to the cytotoxicity with the aid of the stem cell tests for detecting teratogenic activity were described by Newall and Beedles, Toxicol. in Vitro 8, 697–701 (1994).

Cytotoxic effects served in all of these tests as a measure for embryocidal properties of teratogenic/embryotoxic substances.

It is noted that ES cells are at this time the most important cell model in the developmental biology, particularly for the construction of transgenic organisms, however, its employment in the reproduction toxicology and gene toxicology is up to now limited.

SUMMARY OF THE INVENTION

Purpose of the Invention

The invention has the object to provide for a routinely employable in vitro test procedure for the detection of chemically induced embryotoxic/teratogenic effects.

The object of the invention resides in developing an in vitro test procedure for the detection of embryotoxic/teratogenic properties of chemical agents relative to embryonic stem (ES) cells or relative to embryonic germ (EG) cells associated with primordial germ cells. The test procedure is to be particularly suited to give indications of possible developmental disturbances and differentiation disturbances during the embryogenesis.

BRIEF DESCRIPTION OF THE INVENTION

According to the present invention there is provided an in vitro test procedure for detecting chemically-induced embryotoxic/teratogenic effects based on differentiated pluripotent embryonic stem (ES) cells or embryonic germ (EG) cells obtained from primordial germ cells of the mouse and rat. The procedure includes the following steps. Stable transgenic ES/EG cell clones are selected. A differentiation-dependent expression of tissue-specific genes of embryonic stem (ES) cell clones or embryonic germ (EG) cell clones is furnished in the presence of teratogenic substances. Said teratogenic substances act at specific times of the in vitro differentiation and subsequent differentiation. A chemically-induced activation, repression or modulation of the tissue-specific genes which influence embryonic development is detected.

Arbitrary reporter genes for the employed construction of the transgenic cell clones, for example LacZ or luciferase, can be brought under the control of the tissue-specific promoters,. which control cell-specific structural genes, transcription factors, or developmental-control genes.

The cell clones can contain the reporter gene LacZ and a neomycin cassette for selecting stable transfectants, as well as promoter sequences of genes, which code characteristic and essential features of the ectodermal and mesodermal line.

The promoters which are used can be promoters which code the tissue-specific genes, such as for example genes which determine the neuronal cardiogenesis, the muscle formation, or the skeletal development, or promoters of other developmental control genes (Hox or Pax-Gene).

The reporter gene constructions can be specifically activated, repressed or modulated in the course of the differentiation by exogenic test substances and the differentiation-dependent expression during the test procedure can be carried out by embryoid body differentiation in different lines.

The expression pattern of the promoter reporter gene constructions can be influenced by activation of chemicals and can be determined with the aid of the X-Gal staining.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

In the accompanying drawings, in which are shown several of the various possible embodiments of the present invention.

DESCRIPTION OF THE INVENTION AND PREFERRED EMBODIMENTS

The invention is realized according to the claims.

Figure 1:
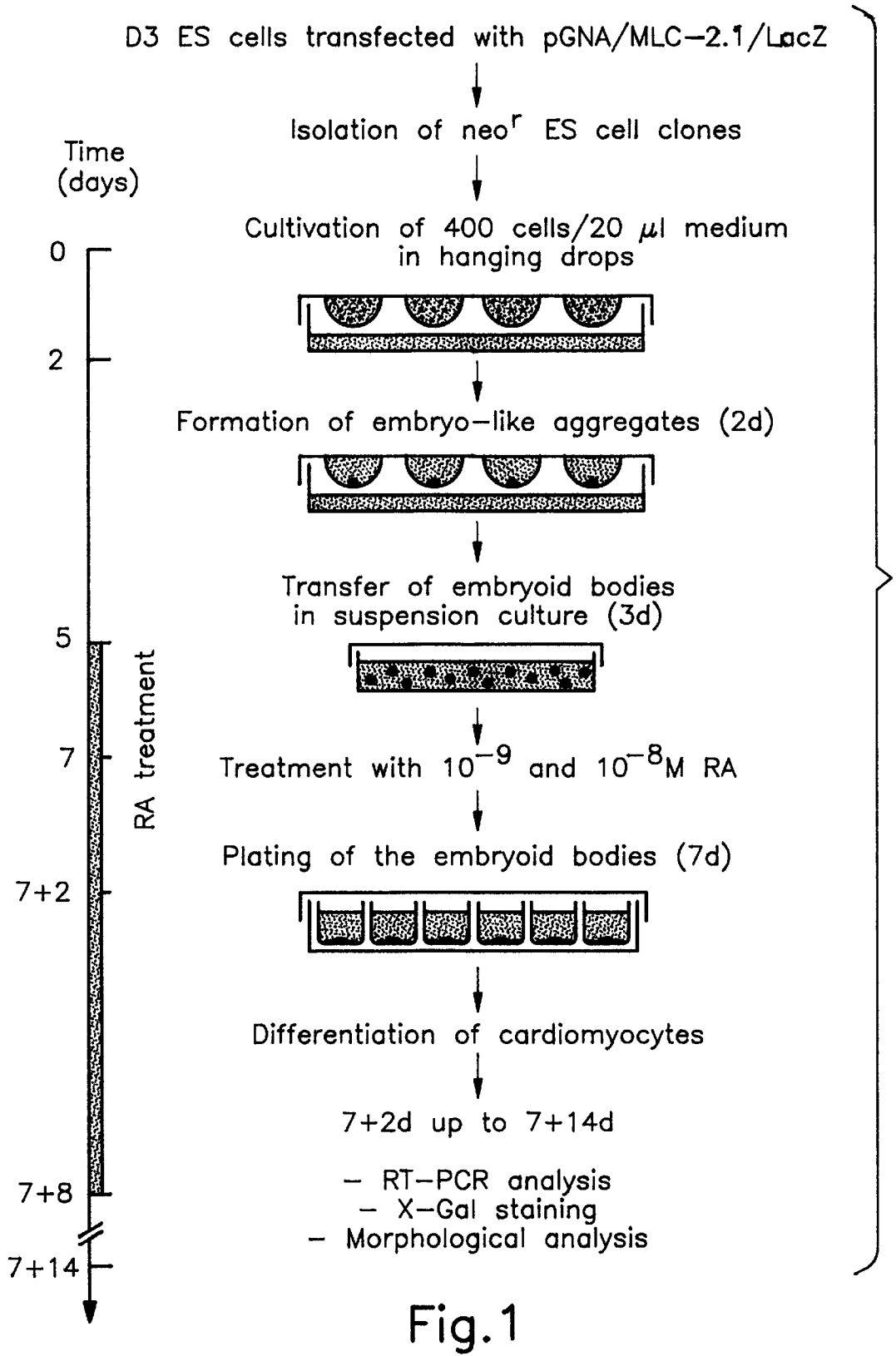
FIG. 1 is a flow chart showing the induction of the differentiation of MLC-2V ES cell clones in cardiomyocytes via embryoid bodies and RA treatment.

Stable transgenic ES or EG stem cell clones are constructed, wherein a bacterial reporter gene LacZ or the luciferase gene is brought under the control of tissue-specific promoters or developmental control genes. Following differentiation of the ES cells in the presence of teratogenic substances into the different germination path derivatives, there occurs a differentiation-dependent expression in the cells, which expresses the tissue-specific promoters. The activation, repression or modulation of these tissue-specific genes is detected based on a simple staining reaction, the X-Gal assay. A battery of relevant test ES cell clones are developed with the invention, wherein the test ES cell clones contain promoter sequences in addition to the reporter gene LacZ (and a neomycin cassette for the selection of stable transfectants), where the promoter sequences regulate characteristic and essential features of the ectodermal and mesodermal line. It should in particular be genes which determine the neuronal, cardiogenic, the muscle, and the skeletal development. Following transfection of these vectors in pluripotent ES/EG cells of the mouse or the rat, stable stem cell clones are selected and these are differentiated after embryoid body development at specific times in the absence of test substances (FIG. 1). Following thereto, the differentiation-dependent expression of the tissue-specific gene can be proven with the aid of the X-Gal staining at different developmental states (while maintaining time and employing vectors suitable therefor). This staining technique can be standardized and can be automated with photometric procedures.

It is possible with this test procedure to detect in vitro chemically-induced changes of the cellular differentiation which occur during the germ-layer differentiation and early embryonic development and lead to developmental disturbances. No live animals but rather permanent cell lines are employed in the test procedure according to the invention.

The substantial advantage of the invention resides in that a standardizable in vitro model is established in a routine screening, wherein the in vitro model leads to a saving of test animals. About 20,000 mammals and birds were used in the field of the reproduction toxicology in Germany per year (1987). Above and beyond this, a large number of mammals are needed for the removal of embryonic organs and tissue (embryonic myocardial cells, limb bud cultures, micromass assay, and the like) such that the total of animal numbers could be at least at 50,000.

With the procedure according to the invention, the following test procedures can in part be replaced or complemented in the pre-screening:

in vivo segment II studies, tests with embryonic organs (limb bud cultures) and primary cultures test procedures with artificial embryos.

The invention is described in detail in the following based on an exemplified embodiment, which exemplified embodiment is however not to limit the application.

EXAMPLE 1

The test procedure is schematically illustrated in FIG. 1. Transgenic ES cell clones, wherein LacZ is expressed under the control of the ventricle-specific MCL-2V promoters (Franz et al., Circ. Res. 73 (1993) 629–638), are used for the examination of such cardiotoxic substances, which lead to developmental disturbances of the heart.

Clones are employed which were transferized or transfected with the vector pGNA-MLC 2.1-LacZ and express MLC-2V in a stable way.

The test substance retinoic acid (RA) is admixed during the mesodermal differentiation in embryoid bodies (for example from day 5 to 15) and subsequently a X-Gal staining of the differentiated embryoid bodies is performed.

Figure 2A:
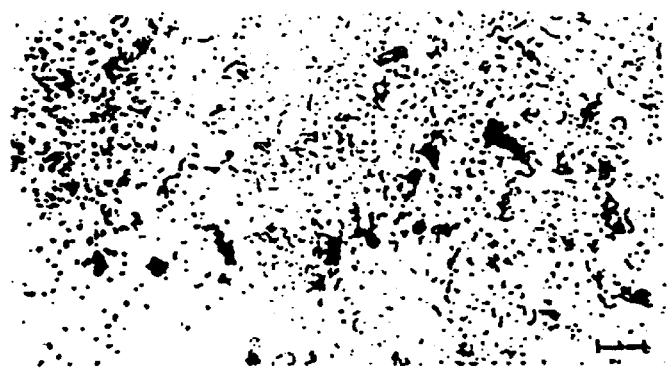
FIG. 2A is a X-Gal staining without induction through the teratogenic substance RA.
Figure 2B:
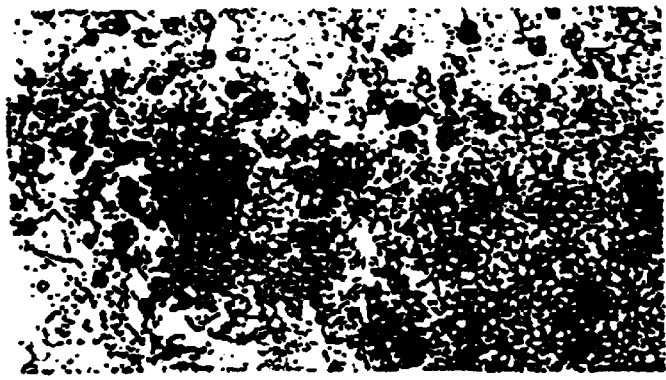
FIG. 2B is an activation of the MLC-2v expression in the MLC clone 3 by $10^{-9}$ after treatment.
Figure 2C:
FIG. 2C is an activation of the MLC-2v expression in the MLC clone 3 by $10^{-8}$ M after treatment.

FIG. 2A, FIG. 2B, and FIG. 2C show the activation of the MLC-2V expression in the MLC clone 3 by $10^{-8}$M, FIG. 2C, and $10^{-9}$M, FIG. 2B, RA after treatment between the 5th and 15th day of the embryoid body differentiation. The control cells FIG. 2A, show X-Gal staining without induction through the teratogenic substance RA.

The vectors were also used for the transfection of EG cells or of ES cells of rats.

We claim:

1. In vitro test procedure for detecting chemically-induced embryotoxic/teratogenic effects based on differentiated pluripotent embryonic stem (ES) cells or embryonic germ (EG) cells obtained from primordial germ cells of a mouse and rat comprising the steps of:

selecting stable transgenic embryonic stem (ES) cell clones or embryonic germ (EG) cell clones containing a construct comprising an arbitrary reporter gene under the control of a tissue specific promoter, furnishing a differentiation-dependent expression of tissue-specific genes of embryonic stem (ES) cell clones or embryonic germ (EG) cell clones in the presence of teratogenic substances, said teratogenic substances acting at specific times of an in vitro differentiation, and subsequent differentiation, and detecting a chemically-induced activation, repression or modulation of the tissue-specific genes which influence embryonic development.

2. In vitro test procedure according to claim 1, wherein arbitrary reporter genes for an employed construction of the transgenic embryonic stem (ES) cell clones or embryonic germ (EG) cell clones are brought under the control of the tissue-specific promoter, which promoter controls cell-specific structural genes, transcription factors, or developmental-control genes.

3. In vitro test procedure according to claim 1 or 2, wherein the cell clones contain the reporter gene LacZ and a neomycin cassette for selecting stable transfectants, as well as promoter sequences of genes, which code characteristic and essential features of the ectodermal and mesodermal line.

4. In vitro test procedure according to claim 1 or 2, wherein promoters which are used are promoters which code the tissue-specific genes, genes which determine neuronal cardiogenesis, muscle formation, or skeletal development, or promoters of other developmental control genes.

5. In vitro test procedure according to claim 1 or 2, wherein reporter gene constructions are specifically activated, repressed or modulated in the course of the differentiation by exogenic test substances and wherein the differentiation-dependent expression during the test procedure is carried out by embryoid body differentiation in different lines.

6. In vitro test procedure according to claim 1 or 2, wherein an expression pattern of promoter reporter gene constructions is influenced by activation of chemicals and is determined with X-Gal staining.

7. In vitro test procedure for detecting chemically-induced embryotoxic/teratogenic effects comprising the steps:

selecting stable transgenic embryonic stem (ES) cell clones or embryonic germ (EG) cell clones containing a construct comprising an arbitrary reporter gene under the control of a tissue specific promoter;

expressing tissue-specific genes of embryonic stem (ES) cell clones or embryonic germ (EG) cell clones differentiation-dependently in the presence of teratogenic substances, wherein said teratogenic substances are acting at specific times of an in vitro differentiation;

subsequently differentiating tissue-specific genes of embryonic stem (ES) cell clones or embryonic germ (EG) cell clones;

detecting chemically-induced activation, repression or modulation of the tissue-specific genes which influence embryonic development; and basing the procedure on differentiated pluripotent embryonic stem (ES) cells or embryonic germ (EG) cells obtained from primordial germ cells of the mouse or rat.

8. In vitro test procedure according to claim 7, further comprising bringing arbitrary reporter genes for a construction of the transgenic cell clones under the control of the tissue specific promoter, which tissue specific promoter controls cell-specific structural genes, transcription factors, or developmental-control genes with stable transgenic embryonic stem (ES) cell clones or embryonic germ (EG) cell clones.

9. In vitro test procedure according to claim 7, wherein the stable transgenic embryonic stem (ES) cell clones or embryonic germ (EG) cell clones contain the reporter gene LacZ and a neomycin cassette for selecting stable transfectants, as well as promoter sequences of genes, which code characteristic and essential features of the ectodermal and mesodermal line.

10. In vitro test procedure according to claim 7, further comprising employing promoters for use as promoters coding the tissue-specific genes, genes which determine the neuronal cardiogenesis, the muscle formation, or the skeletal development, or promoters of other developmental control genes.

11. In vitro test procedure according to claim 7, further comprising specifically activating, repressing or modulating reporter gene constructions in the course of the differentiation by exogenic test substances; and carrying the differentiation-dependent expression out during the test procedure by embryoid body differentiation in different lines.

12. In vitro test procedure according to claim 7, further comprising influencing the expression pattern of promoter reporter gene constructions by activation of chemicals;

determining an expression pattern of the promoter reporter gene constructions with the aid of X-Gal staining.

13. In vitro test procedure according to claim 7, further comprising constructing stable transgenic embryonic stem (ES) cell clones or embryonic germ (EG) cell clones, selecting from among the stable transgenic embryonic stem (ES) cell clones or embryonic germ (EG) cell clones;

expressing tissue-specific genes of embryonic stem (ES) cell clones or embryonic germ (EG) cell clones in vitro differentiation-dependent in the presence of embryotoxic or teratogenic chemical substances;

detecting an embryotoxic or teratogen-induced activation, repression or modulation of tissue-specific genes, which influence embryonic development.

14. In vitro test procedure according to claim 13, further comprising containing an arbitrary reporter gene LacZ and a neomycin cassette for selection-stable transfectants in the embryonic stem (ES) cell clones or embryonic germ (EG) cell clones; and bringing a bacterial reporter gene LacZ under the control of tissue-specific promoters or developmental control genes.

15. In vitro test procedure according to claim 13, further comprising determining a neuronal cardiogenesis, muscle formation, of the skeletal development, or promoters of other developmental control genes with stable transgenic embryonic stem (ES) cell clones or embryonic germ (EG) cell clones.

16. In vitro test procedure according to claim 13, further comprising
specifically activating, repressing or modulating the reporter gene constructions in the course of the differentiation by exogenic test substances.

17. In vitro test procedure according to claim 13, further comprising
carrying out the differentiation-dependent expression during the test procedure by embryoid body differentiation.

18. In vitro test procedure according to claim 8, wherein the arbitrary reporter genes for a construction of the transgenic cell clones are selected from the group consisting of LacZ, luciferase, and mixtures thereof.

19. In vitro test procedure for detecting chemically-induced embryotoxic/teratogenic effects based on differentiated pluripotent embryonic stem (ES) cells or embryonic germ (EG) cells obtained from primordial germ cells of the mouse and rat, comprising the steps of:
selecting stable transgenic embryonic stem (ES) cell clones or embryonic germ (EG) cell clones, wherein arbitrary reporter genes for a construction of the transgenic cell clones are brought under the control of tissue-specific promoters, which control cell-specific structural genes, transcription factors, or developmental-control genes;
furnishing a differentiation-dependent expression of tissue-specific genes of embryonic stem (ES) cell clones or embryonic (EG) cell clones in the presence of teratogenic substances, said teratogenic substances acting at specific times of an in vitro differentiation, and subsequent differentiation; and
detecting a chemically-induced activation, repression or modulation of the tissue-specific genes which influence embryonic development.

\* \* \* \* \*